United States Patent [19]

Anderson

[11] 4,321,823

[45] Mar. 30, 1982

[54] AQUATIC SEDIMENT AND CURRENT MONITOR

[76] Inventor: Roger Y. Anderson, 3201 Campus Blvd., NE., Albuquerque, N. Mex. 87106

[21] Appl. No.: 158,507

[22] Filed: Jun. 11, 1980

[51] Int. Cl.³ .............................................. G01N 1/20
[52] U.S. Cl. ..................................... 73/61.4; 222/57
[58] Field of Search ................ 73/61.4, 61 R, 170 A, 73/171, 189; 222/57

[56] References Cited

U.S. PATENT DOCUMENTS 3,642,171 2/1972 Ernst .................................. 222/57 X
3,715,913 2/1973 Anderson ........................... 73/61 R Primary Examiner—Kyle L. Howell
Assistant Examiner—Joseph W. Roskos
Attorney, Agent, or Firm—Philip M. Hinderstein

[57] ABSTRACT

An aquatic sediment and current monitor adapted to be positioned in a body of water comprising an elongate, vertically alignable, collecting tube having an open upper end and a closed lower end for collecting, over a long period of time, the natural materials and polluting substances that accumulate in the body of water. A generally funnel-shaped magnifying cone is positioned with the small diameter end thereof extending into the open end of the collecting tube to magnify the amount of sediment and pollution collected. A baffle is positioned in the magnifying cone adjacent the large diameter end thereof. A marking material dispenser is provided for automatically marking, at regular intervals, the quantity of sediment and pollution accumulated in the collecting tube during such intervals. A current wheel is positioned above the baffle for measuring the velocity of currents in the water body. A marking material dispenser is also provided for automatically marking the quantity of sediment accumulated in the collecting tube after a predetermined flow of current passed the monitor.

11 Claims, 3 Drawing Figures

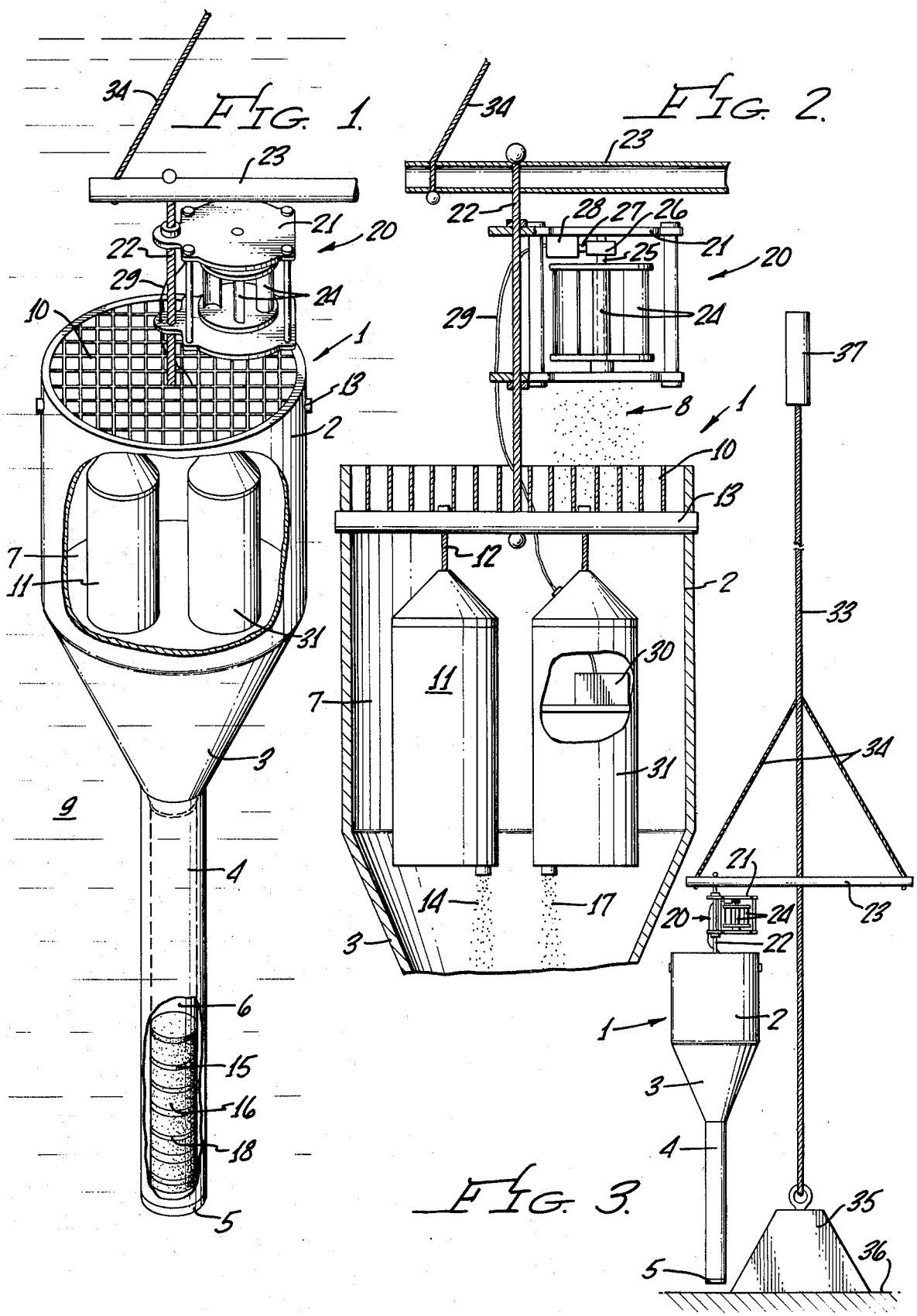

AQUATIC SEDIMENT AND CURRENT MONITOR

BACKGROUND OF THE INVENTION

1. Field of the Invention

The present invention relates to the measurement of currents and their effects upon sediments in bodies of water, such as the ocean, lakes, estuaries, lagoons and reservoirs and, more particularly, to apparatus to be positioned in a body of water for collecting data about currents and sediments and associated pollution.

2. Description of the Prior Art

The measurements of currents in bodies of water and the effects these currents have an erosion and the suspension, transportation, and deposition of sediments is a matter of great importance to the investigation of many problems related to human activity. The dumping of numerous waste forms in shallow water, as well as dredging and other engineering activities, places large quantities of sediment and polluting substances in suspension. These substances are subsequently carried away to different parts of the water body by the actions of currents. Many problems related to waste disposal, channel and harbor dredging, offshore drilling and other engineering projects require detailed knowledge of the motion of suspended sediments and materials and the effects of currents upon sediment movement.

Present aquatic current measuring systems have significant limitations. The most common system uses a propeller or vane-type current meter and means such as a magnetic tape or other recording device for recording the number of revolutions of the propeller. The record is then recovered and processed electronically to determine current velocity. However, no record of the composition, texture, or volume of sediment carried by the currents is collected or measured by such devices. The only permanent information obtained is a magnetic tape or other record. No physical material or substance is obtained from the water body to show the actual response of the water mass to current activity.

SUMMARY OF THE INVENTION

According to the present invention, there is provided apparatus which overcomes the problems discussed above with respect to prior art systems. According to the present invention, water current informtion is obtained simultaneously with a record of the composition, texture and volume of sediment carried by the measured currents. That is, a collecting vessel is adapted to be positioned in a body of water and left there to collect a continuous record of suspended matter and sediment carried past the vessel by water currents, thereby eliminating the problem of obtaining a permanent record of the material carried by the currents. The present structure also includes apparatus for magnifying the rate of accumulation of current-supplied materials, thereby assuring that adequate material is contained in the permanent record. The present invention also includes apparatus for measuring the velocity of the currents and recording this information directly in the permanent record of accumulated sediments. As a result in the permanent record of accumulated sediments. As a result, the present device not only collects the sediment carried by the currents, but also measures the velocity of the current that was responsible for carrying a particular type, size or volume of sediment. Accordingly, the present invention makes it possible to accurately determine the volume, composition and rate of suspension, transportation and deposition of sediments carried by currents of differet sources and velocities to thereby determine the environmental effects of human activites, as well as the behavior of the natural environment.

Briefly, the present aquatic sediment and current monitor comprises an elongate, vertically alignable, collecting tube having an open upper end and a closed lower end, a generally funnel-shaped magnifying cone positioned with the small diameter end thereof extending into the open end of the collecting tube, baffle means positioned adjacent the large diameter end of the magnifying cone for minimizing turbulence in the collecting tube and for preventing entrance into the collecting tube of large organisms while allowing solids and small organisms to enter the collecting tube, means for automatically marking, at regular intervals, the quantity of sediment accumulated in the collecting tube during such intervals, a current measuring device for measuring current flow passed the monitor, and means responsive to the current measuring device for automatically marking the quantity of sediment accumulating in the collecting tube after movement of a predetermined flow of current passed the monitor.

OBJECTS, FEATURES AND ADVANTAGES

It is therefore an object of the present invention to solve the problems encountered heretofore with the measurement of currents in water bodies. It is a feature of the present invention to solve these problems by simultaneously collecting data about currents and the composition, texture or volume of sediment carried by such currents. An advantage to be derived is the obtaining of a permanent record of the materials carried by currents. Another advantage is that the current velocity information is recorded directly in the permanent record of accumulated sediments. Still another advantage is that is is possible to accurately determine the volume, composition and rate of suspension, transportation and deposition of sediments carried by currents of different sources and velocities. Another advantage is the ability to determine the environmental effects of human activities, as well as the behavior of the natural environment on water bodies.

Still other objects, features and attendant advantages of the present invention will become apparent to those skilled in the art from a reading of the following detailed description of the preferred embodiment constructed in accordance therewith, taken in conjunction with the accompanying drawings wherein like numerals designate like parts in the several figures and wherein:

BRIEF DESCRIPTION OF THE DRAWINGS

FIG. 1 is a perspective view, partly cut away, of an aquatic sediment and current monitor constructed in accordance with the teachings of the present invention;

FIG. 2 is an enlarged side elevation view, partly in section, of the apparatus of FIG. 1; and FIG. 3 is a front elevation view of a preferred embodiment of apparatus for mounting and supporting the apparatus of FIG. 1 in a body of water.

DESCRIPTION OF THE PREFERRED EMBODIMENT

Referring now to the drawings, there is shown an aquatic sediment and current monitor, generally designated 1, which has many components in common with the aquatic sediment and pollution monitor described and claimed in my prior U.S. Pat. No. 3,715,913. More specifically, monitor 1 includes a collecting tube 6 having an open upper end and a closed lower end for collecting and storing, over a relatively long period of time, aquatic sediment and pollutants. Collecting tube 6 is positioned within a housing tube 4 which is sealed at its open lower end by a threaded cap 5. The open upper end of housing tube 4 receives and is connected adjacent the small diameter end of a magnifying cone 3. The small diameter end of magnifying cone 3 extends into collecting tube 6 which is held in position by threaded cap 5.

Connected to, and preferably made integral with, the upper, large diameter end of magnifying cone 3 is a hollow housing 2 which defines an entry chamber 7 for monitor 1. The upper end of housing 2 is open and positioned to receive the materials and substances 8 suspended in a body of water 9 by the currents passing monitor 1. Such materials and substances pass through chamber 7 and magnifying cone 3 into collecting tube 6 where they are stored as a permanent material record for analysis at a later time.

In order to control the effects of currents on the passage of materials and substances 8 into chamber 7 and collecting tube 6, chamber 7 has preferably positioned therein, at the upper end thereof, a cell-like network of baffles 10. Baffles 10 cause the open end of chamber 7 to behave as a surface over which currents flow essentially without turbulence at the same time that suspended materials 8 move down through the cells of baffle 10 for settling in collecting tube 6.

According to the preferred embodiment of the present invention, mounted within entry chamber 7 is a marking material dispenser 11 for automatically marking, at regular intervals, the quantity of sediment accumulated in collecting tube during such intervals. Marking material dispenser 11 may be of the type described in my prior U.S. Pat. No. 3,715,913. Alternatively, and preferably, marking material dispenser 11 is of the type described in my co-pending U.S. patent application Ser. No. 158,508, filed concurrently herewith. Dispense 11 may be suspended by a cable 12 from a mounting rod 13 which extends across and through housing 2, beneath baffles 10. As will be discussed in greater detail hereinafter, dispenser 11 contains an inert marking material 14 having a density greater than water. At selected intervals, marking material 14 is dispensed from dispenser 11 so that it may settle in collecting tube 6 to provide layers 15 of marking material 14 between layers 16 of sediment 8.

Monitor 1 further includes a commercially available current measuring device, generally designated 20, such as a Savonius rotor. More specifically, current measuring device 20 includes a frame 21 attached to a mounting line 22 connected between mounting rod 13 and a mounting bar 23. Device 20 also includes a rotor 24 mounted for rotation with a shaft 25. Also mounted on shaft 25 is a switch actuator 26 which cooperates with the arm 27 of a switch 28. Thus, when water currents cause rotation of rotor 24, switch actuator 26 is also rotated so as to activate switch 28 for every rotation of shaft 25. The output of switch 28 is conducted over electrical lines 29 to a counter 30 positioned within a marking material dispenser 31. Marking material dispenser 31 is identical to marking material dispenser 11; except that the control circuitry of marking material dispenser 11 which causes the dispensing of marking material 15 at time intervals is replaced by counter 30.

Each rotation of rotor 24 closes an electrical circuit in switch 28. Each closure of the circuit in switch 28 is transmitted by lines 29 to counter 30 which may be a commercially available events counter. Events counter 30 is pre-set to actuate marking material dispenser 31 after a fixed number of revolutions of rotor 24.

The complete operation of monitor 1 may be best understood with reference to FIGS. 1 and 2. More specifically, marking material dispenser 31 contains an inert marking material 17 such as plastic granule with a density greater than water. Suspended natural materials and polluting substances 8 in water body 9 carried to monitor 1 by currents pass by gravity through baffles 10 into collecting chamber 7 and around dispensers 11 and 31 into collecting tube 6 where it settles as a layer 16 of sediment 8. Rotation of rotor 24 closes switch 28 with each revolution and the electrical pulse is transmitted by electrical lines 29 to event counter 30 in marking material dispenser 31. After a fixed and pre-set number of pulses are counted by event counter 30, event counter 30 transmits a signal to the motor (not shown) in dispenser 31 which causes rotation of the magazine (not shown) therein which releases marking material 17 into magnifying cone 3 where it is deflected into collecting tube 6. Such marking material 17 settles as a distinct layer 18 on the upper surface of the previously deposited layer 16 of sediment 8. Accordingly, the number of layers 18 of marking material 17 emplaced in collecting tube 6 is determined by the number of revolutions of rotor 24 which is determined by the velocity of the currents. The materials and substances 8 in collecting tube 6 provide a permanent record of the composition, texture and volume of sediment 8 carried past monitor 1 by such currents. The velocity of the currents is calculated by determining the number of revolutions of rotor 10 represented by the number of layers 18 of marking material 17 emplaced in collecting tube 6 during a fixed and known time interval.

In order to establish such a fixed and known time interval, monitor 1 preferably includes marking material dispenser 11. Dispenser 11 automatically releases alternate marking material 14 at pre-set and regular intervals upon command from a commercially available electronic timer contained therein, as described more fully in my prior U.S. Pat. No. 3,715,913 and my co-pending patent application file concurrently herewith. The alternate marking material 14, upon release from dispenser 11, settles by gravity into collection tube 6 where it forms a distinct layer 15 of alternate marking material 14 at the upper surface of collected sediment 8. Accordingly, the accuracy and effectiveness of monitor 1 during prolonged periods of operation is increased by providing multiple periods of time for which current velocity may be calculated.

Referring now to FIG. 3, monitor 1 may be suspended by mounting line 22 from mounting bar 23 which is affixed to a main cable 33 and secured by stabilizing cables 34. Main cable 33 may be suspended between an anchor 35 on the floor 36 of water body 9 and a buoy 37 floating on or within water body 9. Recovery of monitor 1 and collecting tube 6 provides a record of the layers of marking material 14 and 17, as well as a material record of the materials and substances 8 carried by the water currents. The material record may be analyzed to deterine the composition, texture and volume of natural and polluting substances carried by the currents. The velocity of the currents associated with the aforementioned substances may be calculated from the number of layers of marking material.

It can, therefore, be seen that in accordance with the present invention, there is provided an efficient apparatus for measuring the velocity of currents and for collecting a permanent material record of sediments carried by such currents. Monitor 1 serves to completely replace the inefficient structures of prior art measuring devices. Not only is monitor 1 more efficient by permitting the collection of information about the velocity of currents without electronic recording instruments, but it has the added advantage of collecting a material record of the sediments carried in suspension by the same currents for which velocity information is collected. By using the sediment carried by the currents as a medium for recording the velocity of the currents and the exact time at which current measurements are made, the prior art technique of recording only the velocity of currents is completely replaced. The increased efficiency of the present invention makes it possible to analyze the material carried by currents and thereby determine the content and source of waste and polluting substances as well as natural materials carried by the currents. The present invention also makes it possible to determine the impact of dredging and engineering activities on environmental systems affected by currents.

While the invention has been described with respect to a preferred physical embodiment constructed in accordance therewith, it will be apparent to those skilled in the art that various modifications and improvements may be made without departing from the scope and spirit of the invention. Accordingly, it is to be understood that the invention is not to be limited by the specific illustrative embodiment, but only by the scope of the appended claims.

I claim:

1. An aquatic sediment and current monitor adapted to be positioned in a body of water comprising:
   an elongate, vertically alignable, collecting tube having an open upper end and a closed lower end for accumulating aquatic sediment;
   means for measuring currents in said body of water; and
   means responsive to said measuring means for automatically marking the quantity of sediment accumulated in said collecting tube after movement of a predetermined current flow past said monitor.

2. An aquatic sediment and current monitor according to claim 1, wherein said marking means comprises:
   a dispensing device containing a marking material; and
   means responsive to said measuring means for activating said dispensing device to release said marking material contained therein, said marking material being conducted into said collecting tube.

3. An aquatic sediment and current monitor according to claim 2, further comprising:
   a generally funnel-shaped magnifying cone positioned with the small diameter end thereof extending into said open end of said collecting tube; and
   baffle means positioned adjacent the large diameter end of said magnifying cone for controlling passage of solids into said collecting tube.

4. An aquatic sediment and current monitor according to claim 3, wherein said measuring means is positioned outside of said magnifying cone and wherein said dispensing device is positioned within said magnifying cone.

5. An aquatic sediment and current monitor according to claim 2, wherein said measuring means comprises:
   a rotatable wheel positionable in said body of water and adapted to be rotated by currents in said body of water; and
   means responsive to the rotation of said wheel for generating electrical signals indicative of the rotation of said wheel.

6. An aquatic sediment and current monitor according to claim 5, wherein said activating means comprises:
   means responsive to said electrical signals for periodically activating said dispensing device after a predetermined number of revolutions of said wheel.

7. An aquatic sediment and current monitor according to claim 1, further comprising:
   means for automatically marking, at regular time intervals, the quantity of sediment accumulated in said collecting tube during such time intervals.

8. An aquatic sediment and current monitor according to claim 7, wherein said current flow marking means comprises:
   a first dispensing device containing a first marking material; and
   means responsive to said measuring means for activating said first dispensing device to release said first marking material contained therein, said first marking material being conducted into said collecting tube.

9. An aquatic sediment and current monitor according to claim 8, wherein said time intervals marking means comprises:
   a second dispensing device containing a second marking material;
   timing means for establishing said time intervals; and
   means responsive to said timing means for periodically activating said second dispensing device to release said second marking material contained therein, said second marking material being conducted into said collecting tube.

10. An aquatic sediment and current monitor according to claim 9, further comprising:
    an elongate, hollow housing, said first and second dispensing devices being positioned within said housing; and
    a generally funnel-shaped magnifying cone positioned with the small diameter end thereof extending into said open end of said collecting tube, the large diameter end of said magnifying cone being connected to the lower end of said housing.

11. An aquatic sediment and current monitor according to claim 10, further comprising:
    baffle means positioned in the upper end of said housing for controlling the passage of solids into said collecting tube.

* * * * *